United States Patent
Zhu et al.

(10) Patent No.: US 7,291,649 B2
(45) Date of Patent: Nov. 6, 2007

(54) FORMING GERMICIDAL AROMATIC DIALDEHYDES WITH ACETALS

(75) Inventors: Peter C. Zhu, Irvine, CA (US); Bobby N. Brewer, Lewis Center, OH (US); Kaitao Lu, Irvine, CA (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 11/172,343

(22) Filed: Jun. 29, 2005

(65) Prior Publication Data

US 2007/0004808 A1    Jan. 4, 2007

(51) Int. Cl.
*A61K 31/11*    (2006.01)
*C07C 47/544*    (2006.01)

(52) U.S. Cl. .......................... 514/693; 514/705; 568/442

(58) Field of Classification Search ...................... None
See application file for complete search history.

(56) References Cited

U.S. PATENT DOCUMENTS

| | | |
|---|---|---|
| 1,901,704 A | 3/1933 | Delles |
| 2,527,533 A | 10/1950 | Copenhaver |
| 3,016,328 A | 1/1962 | Pepper et al. |
| 3,102,811 A | 9/1963 | Barney |
| 3,229,851 A | 1/1966 | Horwitt et al. |
| 3,474,176 A | 10/1969 | Freeman |
| 3,763,900 A | 10/1973 | Solms-Baruth et al. |
| 3,912,450 A | 10/1975 | Boucher |
| 3,929,662 A | 12/1975 | Boucher |
| 3,968,248 A | 7/1976 | Boucher |
| 3,968,250 A | 7/1976 | Boucher |
| 4,244,876 A | 1/1981 | Warner et al. |
| 4,418,055 A | 11/1983 | Andersen et al. |
| 4,419,368 A | 12/1983 | Jones et al. |
| 4,436,754 A | 3/1984 | Jacobs |
| 4,448,977 A | 5/1984 | Warner et al. |
| 4,592,892 A | 6/1986 | Ueno et al. |
| 4,690,772 A | 9/1987 | Tell |
| 4,698,312 A | 10/1987 | Wong et al. |
| 4,831,449 A | 5/1989 | Kimura |
| 4,847,304 A | 7/1989 | Bruckner et al. |
| 4,851,449 A | 7/1989 | Bruckner et al. |
| 4,971,999 A | 11/1990 | Bruckner et al. |
| 5,107,032 A | 4/1992 | Erb et al. |
| 5,128,051 A | 7/1992 | Theis et al. |
| 5,192,459 A | 3/1993 | Tell et al. |
| 5,250,160 A | 10/1993 | Oksman |
| 5,338,532 A | 8/1994 | Tomalia et al. |
| 5,389,685 A | 2/1995 | Smith et al. |
| 5,424,323 A | 6/1995 | Wachman et al. |
| 5,429,797 A | 7/1995 | Camiener |
| D363,019 S | 10/1995 | Arnold et al. |
| 5,494,637 A | 2/1996 | Barlow |
| 5,540,326 A | 7/1996 | Arnold et al. |
| 5,558,841 A | 9/1996 | Nakagawa et al. |
| 5,567,385 A | 10/1996 | Miller et al. |
| 5,662,941 A | 9/1997 | Bourbon et al. |
| 5,700,377 A | 12/1997 | Cox |
| 5,761,069 A | 6/1998 | Weber et al. |
| 5,800,838 A | 9/1998 | Bourbon et al. |
| 5,863,547 A | 1/1999 | Miner |
| 5,866,723 A | 2/1999 | Hamper et al. |
| 5,874,637 A * | 2/1999 | Giselbrecht et al. ......... 568/430 |
| 5,936,001 A | 8/1999 | Block |
| 5,945,451 A | 8/1999 | Kraatz et al. |
| 6,071,972 A | 6/2000 | Block |
| 6,080,789 A | 6/2000 | Lutz |
| 6,096,698 A | 8/2000 | Milling |
| 6,270,784 B1 | 8/2001 | Mrusek et al. |
| 6,297,285 B1 | 10/2001 | Lutz |
| 6,309,658 B1 | 10/2001 | Xia et al. |
| 6,458,554 B1 | 10/2002 | Hui et al. |
| 6,461,997 B1 | 10/2002 | Hegde et al. |
| 6,552,203 B2 | 4/2003 | Bertenshaw et al. |
| 2001/0053333 A1 | 12/2001 | Messier et al. |
| 2004/0071592 A1 | 4/2004 | Annis |

FOREIGN PATENT DOCUMENTS

| | | |
|---|---|---|
| DE | 2002-10255647 | 11/2002 |
| EP | 0292300 | 11/1988 |
| EP | 0292301 | 11/1988 |
| EP | 0552853 | 7/1993 |
| EP | 0 292 300 A2 | 11/1998 |
| JP | 36000752 | 4/1957 |
| JP | 49035383 | 8/1972 |
| JP | 09124538 | 5/1997 |
| JP | 11140040 | 5/1999 |

(Continued)

OTHER PUBLICATIONS

Advanced Sterilization Products, "CIDEX® OPA Solution, And Speed Has Its Advantages", (2001),1.

(Continued)

*Primary Examiner*—Sikarl A. Witherspoon (57) ABSTRACT

Methods of forming germicidal aromatic dialdehydes by hydrolyzing acetals are disclosed. Compositions and kits including both germicidal aromatic dialdehydes and acetals that are capable of being converted to germicides are disclosed. In one aspect, an acetal may be converted to germicide gradually in a deployed germicidal solution to accommodate for loss of the germicide or otherwise to modify the germicidal efficacy of the deployed germicidal solution.

38 Claims, 1 Drawing Sheet

FOREIGN PATENT DOCUMENTS

| JP | 2003081962 | 9/2001 |
|---|---|---|
| RU | 2020964 | 10/1994 |
| SU | 1395329 | 5/1988 |
| WO | WO 95/16023 | 6/1995 |
| WO | WO-9516023 | 6/1995 |
| WO | WO-0024761 | 5/2000 |

OTHER PUBLICATIONS

Advanced Sterilization Products, "CIDEX® OPA Solution", http://www.cidex.com/products_&_services/cidex/cidex_opa/index/asp, retrieved Aug. 7, 2003,(2003),1-2.

Advanced Sterilization Products, "CIDEX® OPA, High Level Disinfecting Solution", *Technical Info.*, (2004),1-4.

Durham, Anthony C., "A Survey of Readily Available Chelators for Buffering Calcium Ion Concentrations in Physiological Solutions", *Cell Calcium 4*, (1983),33-46.

Kuronuma, Hiroshi , "Stability of Ortho-Phthalaldehyde Solutions Under Various Storage Conditions", *Journal of Japanese Society of Hospital Pharmacists*, vol. 36, No. 1, (2000),55-58.

Li, Mingwei , et al., "Preparation of Aromatic Polyaldehydes by Hydrosis of Gem-Dibromides", *Beijing No. 1 Light Ind. Indst., Beijing, Peoples Republic of China Huaxue Chiejie*, 26(5). Journal written in Chinese (Abstract Translated),(1985),168-170.

Mislow, Kurt , et al., "Optical Resolution of a 1, 2, 5, 6-Dibenzcyclooctatetraene Derivative", *Journal of the American Chemical Society* , vol. 84, (Aug. 3, 1962),3591-3592.

Power, E.G.M. , "Spricidal Action of Alkaline Glutaraldehyde: Factors Influencing Activity and a Comparison With Other Aldehydes", *Journal of Applied Bacteriology*, (1990),261-268.

Rehn, D. , et al., "About the Antimicrobial Activity of Substituted Aromatic Aldehydes", *Zbl. Bakt. Hyg: I. Abt. Orig.*, vol. B172, tables 1, 2, XP002325401,(1981),508-519.

Rubbo, S.D. , "Biocidal Activites of Glutaraldehyde and Related Compounds", *Symposium of Chemical Disinfection: Paper VIII, J. Appl. Bact.* 30(1), (1967),78-87.

Sagripanti, Jose-Luis , "Effects of Salt and Serum on the Spricidal Activity of Liquid Disinfectants", *Journal of AQAC International*, vol. 80, No. 6, (1997),1198-1207.

Setlow, B. , "Mechanisms of Killing Spores of *Bacillus subtilis* by Acid, Alkali and Ethanol", *Journal of Applied Microbiology* (92), (2002),362-375.

Makin, S.M., et al., "Synthesis of acetals of glutaric and glutaconic aldehydes from alkoxypyrans," Moscow Institute of Fine Chemical Tech., vol. 3, No. 8, pp. 1381-1384, Aug. '67.

Hall & Howe, "Acetals of Glutardialdehyde, etc.," Journal of the Chemical Society (1951), pp. 2480-2483.

Botteghi, et al., "Malonaldehyde, Succinaldehyde and Glutaraldehyde Monoacetals: Syntheses and Applications," Instituto de Chimica Applicata, pp. 592-604, 1985.

Yanovskaya, et al., "Hydrolysis of Some Bisacetals of Dialdehydes," N.D. Zelinskii Institute of Organic Chemistry, No. 11, pp. 1999-2001, Nov. 1964.

Advanced Sterilization Products, "CIDEX OPA Solution", http://www.cidex.com/products_&_services/cidex/cidex_opa/index/asp, retrieved Aug. 7, 2003,(2003), pp. 1-2.

Advanced Sterilization Products, "CIDEX OPA Solution, And Speed Has Its Advantages", (2001), 1 page.

Advanced Sterilization Products, "CIDEX OPA, High Level Disinfecting Solution", *Technical Info.*, (2004), pp. 1-4.

Durham, Anthony C., "A Survey of Readily Available Chelators for Buffering Calcium Ion Concentrations in Physiological Solutions", *Cell Calcium 4*, (1983), pp. 33-46.

Kuronuma, Hiroshi, "Stability of Ortho-Phthalaldehyde Solutions Under Various Storage Conditions", *Journal of Japanese Society of Hospital Pharmacists*, vol. 36, No. 1, (2000), pp. 55-58.

Li, Mingwei , et al., "Preparation of Aromatic Polyaldehydes by Hydrosis of Gem-Dibromides", *Beijing No. 1 Light Ind. Indst., Beijing, Peoples Republic of China Huaxue Chiejie*, 26(5). Journal written in Chinese (Abstract Translated),(1985), pp. 168-170.

Mislow, Kurt , et al., "Optical Resolution of a 1, 2, 5, 6-Dibenzcyclooctatetraene Derivative", *Journal of the American Chemical Society* , vol. 84, (Aug. 3, 1962), pp. 3591-3592.

Power, E.G.M. , "Sprocidal Action of Alkaline Glutaraldehyde: Factors Influencing Activity and a Comparison With Other Aldehydes", *Journal of Applied Bacteriology*, (1990), pp. 261-268.

Rehn, D. , et al., "About the Antimicrobial Activity of Substituted Aromatic Aldehydes", *Zbl. Bakt. Hyg: I. Abt. Orig.*, vol. B172, tables 1, 2, XP002325401,(1981), pp. 508-519.

Rubbo, S.D. , "Biocidal Activites of Glutaraldehyde and Related Compounds", *Symposium of Chemical Disinfection: Paper VIII, J. Appl. Bact.* 30(1), (1967), pp. 78-87.

Sagripanti, Jose-Luis , "Effects of Salt and Serum on the Spricidal Activity of Liquid Disinfectants", *Journal of AQAC International*, vol. 80, No. 6, (1997), pp. 1198-1207.

Setlow, B. , "Mechanisms of Killing Spores of *Bacillus subtilis* by Acid, Alkali and Ethanol", *Journal of Applied Microbiology* (92), (2002), pp. 362-375.

* cited by examiner

FIG. 1

FORMING GERMICIDAL AROMATIC DIALDEHYDES WITH ACETALS

BACKGROUND

1. Field

Various embodiments of the invention relate to germicidal compositions, methods and kits for preparing the germicidal compositions, and methods of using the compositions and kits for disinfection or sterilization.

2. Background Information

Various aldehyde-based germicidal compositions are known in commerce and have been discussed in the literature. Among the more prevalent of the aldehyde-based germicidal compositions are those including o-phthalaldehyde (OPA; also referred to simply as phthalaldehyde).

OPA has a number of characteristics that make it well suited as a germicide. For instance, OPA is generally not regarded to be carcinogenic, is substantially odorless, and has rapid germicidal action. i-Phthalaldehyde (IPA) and t-phthalaldehyde (TPA) also have germicidal efficacy, although typically not as great as that of OPA. IPA may also enhance the germicidal efficacy of OPA.

However, OPA as an aldehyde may gradually undergo oxidation reactions to form the carboxylic acids 2-formyl-benzoic acid and/or phthalic acid when exposed to air or oxygen, as shown by the following reaction:

Over time, such as, for example, during prolonged periods of storage, such oxidation reactions may consume OPA, and may tend to decrease germicidal efficacy and/or lifetime of germicidal compositions. Approaches for dealing with such oxidation of OPA would be useful.

BRIEF DESCRIPTION OF THE SEVERAL VIEWS OF THE DRAWINGS

The invention may best be understood by referring to the following description and accompanying drawings that are used to illustrate embodiments of the invention. In the drawings.

DETAILED DESCRIPTION

In the following description, numerous specific details are set forth. However, it is understood that embodiments of the invention may be practiced without these specific details. In other instances, well-known structures and techniques have not been shown in detail in order not to obscure the understanding of this description.

I. Introduction

The inventors have conceived of the idea of using an acetal to form a germicidal aromatic dialdehyde. Acetals tend to be more stable toward oxidation than dialdehydes. The germicidal aromatic dialdehyde, once formed, may be used as an active ingredient in a germicidal solution for disinfection, sterilization, or otherwise killing germs, or other microorganisms. In addition, acetals may be converted to germicides gradually in a deployed germicidal solution to replenish lost germicide or otherwise maintain an effective germicidal concentration.

II. Exemplary Germicidal Aromatic Aldehydes

Various suitable germicidal aromatic dialdehydes are known in the arts. One suitable germicidal aromatic dialdehyde is o-phthalaldehyde (OPA). OPA is also known as 1,2-benzenedicarboxaldehyde or sometimes simply referred to as phthalaldehyde. OPA is a germicidal aromatic dialdehyde having the following structure:

Other suitable germicidal aromatic dialdehydes include isomers of OPA. One suitable isomer is IPA. IPA is also known as 1,3-benzenedicarboxaldehyde or simply isophthalaldehyde. Another suitable isomer is t-phthalaldehyde (TPA). TPA is also known as 1,4-benzenedicarboxaldehyde or simply terephthalaldehyde. OPA, IPA, and TPA are commercially available from numerous sources including Sigma-Aldrich, Alfa Aesar, and Fluka, among others.

Still other suitable germicidal aromatic dialdehydes include various 4-halo-phthalaldehydes having the following generalized structure:

where X is a halogen, such as fluorine, chlorine, bromine, or iodine. Specific examples of 4-halo-phthalaldehydes that are suitable include 4-fluoro-phthalaldehyde, 4-chloro-phthalaldehyde, 4-bromo-phthalaldehyde, and 4-iodo-phthalaldehyde. Corresponding 3-halo-phthalaldehydes are also suitable. Further details of such germicides, if desired, including possible synthesis methods, also described in U.S. Pat. No. 6,891,069, entitled "SYNTHESIS OF 4-SUBSTITUTED PHTHALALDEHYDE", which is assigned to the Assignee of the present application.

Additional suitable germicidal aromatic dialdehyes include various propanedials having the following generalized structure:

wherein Ar is an aryl group. The carbons of the aldehyde groups of the structure immediately above are not directly attached to the aromatic ring structure, unlike those of others disclosed herein, such as, for example, OPA. Specific suitable germicidal aromatic dialdehydes include phenyl-pro- panedial, 3-(1-formyl-2-oxoethyl)-2-nitro-benzoic acid, 4-pyrimidinyl-propanedial, 2-Benzoxazolyl-propanedial, (4-Methoxyphenyl)-propanedial, and 2-Pyridinyl-propanedial. Phenyl-propanedial is available from Matrix Scientific, of Columbia, S.C. 3-(1-Formyl-2-oxoethyl)-2-nitro-benzoic acid is available from Acros Organics and Matrix Scientific. 4-Pyridinyl-propanedial is available from AKos Building Blocks, Acros Organics, of Loughborough, Leicestershire, United Kingdom, and Matrix Scientific. 2-Benzoxazolyl-propanedial is available from Acros Organics and Matrix Scientific. (4-Methoxyphenyl)-propanedial is available from Matrix Scientific. 2-Pyridinyl-propanedial is available from Acros Organics and Matrix Scientific. Further details of such germicides, if desired, are described in U.S. Pat. No. 6,891,069.

Now, these are just a few examples of suitable germicidal aromatic dialdehydes. The scope of the invention is not limited to just these particular examples.

III. Forming Germicidal Aromatic Aldehydes From Acetals

A method, according to one or more embodiments of the invention, may include forming a germicidal aromatic dialdehyde, such as, for example, one of the germicidal aromatic dialdehydes disclosed above, from an acetal. In one or more embodiments of the invention, the germicidal aromatic dialdehyde may be formed by hydrolyzing or otherwise reacting the acetal in an aqueous medium, such as, for example, an aqueous germicidal solution.

For instance, consider the following somewhat generalized reaction of acetals to form germicidal aromatic dialdehydes, such as, for example, OPA and/or OPA derivatives:

Acetal    Germicidal aromatic dialdehyde

In this reaction, the acetal reactant is converted to the germicidal aromatic dialdehyde product. The reaction generally takes place in the presence of water, such as, for example, in an aqueous solution, and may optionally be catalyzed or otherwise promoted by the inclusion of an acid.

Characteristics of the acetal reactant that distinguish or identify it as an acetal include that it has two —OR or —OAr groups bonded to the same carbon, where the O represents oxygen, the R represents an aliphilic group, and the Ar represents an aromatic group. In particular, the illustrated acetal is a diacetal that includes a cyclic phthalan structure. The cyclic phthalan structure includes a first carbon with two —OR groups bonded thereto and a second carbon with two —OR groups bonded thereto, where an oxygen is bonded to both of the first and second carbons.

The illustrated reaction is a generalized reaction in which the X may include a 3- or 4-position hydrogen, halogen (for example fluorine, chlorine, bromine, or iodine), very short chain alkoxy (for example methoxy, ethoxy, pentoxy, etc.), or the like, as long as the product aromatic dialdehyde has useful germicidal efficacy. In the special case where X is hydrogen, the product germicidal aromatic dialdehyde is OPA, and the possible starting acetals, such as, for example, various 1,3-dialkoxyphthalalans, may be referred to herein collectively as "OPA acetals".

Suitable R groups, according to various embodiments of the invention, include, but are not limited to, short or very short chain straight or branched alkyl groups, and solubility enhancing groups, such as, for example, glycol, polyethylene glycol, and other oxygenated polymer groups or moieties. The R groups may either be the same or different and may be selected independently of one another, if desired.

As used herein, short chain straight or branched alkyl groups refers to groups having from 1 to 10 carbons, and very short chain straight or branched alkyl groups refers to groups having from 1 to 5 carbon atoms. Representative suitable alkyl groups include, but are not limited to, methyl, ethyl, propyl, isopropyl, butyl, isobutyl, pentyl, and isopentyl. Groups having more than 10 carbons are also potentially suitable but may tend to significantly decrease the solubility of the acetals in aqueous solution.

If desired, in one or more embodiments of the invention, the acetal may include a solubility enhancing group as an R group. Glycol is one example of a solubility enhancing group. Polyethylene glycol is another example of a solubility enhancing group. Polyethylene glycol (PEG) is a polymer, in particular a polyether. The PEG group may have various molecular weights, such as, for example, an average molecular weight of about 200, in one instance. In one or more embodiments of the invention, long-chain PEG dialcohol molecules may be reacted with a starting germicidal aromatic dialdehyde compound in order to form the corresponding acetal with improved aqueous solubility. The addition of a PEG group or moiety to another molecule is sometimes referred to in the arts as pegylation, and the resulting molecule is sometimes referred to as pegylated. Accordingly, an acetal according to one or more embodiments of the invention, may be a pegylated acetal that is capable of reacting to form an un-pegylated germicidal aldehyde compound. Inclusion of such solubility enhancing groups may help to increase the solubility of the acetal in hydrophilic media, such as, for example, aqueous solutions.

By way of example, representative suitable acetals include the following:

where Me is methyl, Et is ethyl, Pr is propyl, Bu is butyl, n may representatively be from about 1 to 10, for instance, and where X may be any of the groups previously described above, such as, for example, a 3- or 4-halogen or very short chain alkoxy.

To further illustrate certain concepts, consider the following somewhat generalized reaction of acetals to form germicidal aromatic dialdehydes, such as, for example, IPA and/or IPA derivatives:

where the X and R groups may include the same groups mentioned above.

The diacetal does not have the cyclic phthalan structure of the OPA acetal disclosed above. This is due to the meta-positioning of the two aldehyde groups. Instead, the diacetal includes two separate acetal functionalities. Accordingly, the acetal may be converted to the germicidal aromatic dialdehyde in two separate staged hydrolysis reactions.

Now, IPA and certain of its derivatives tend to be poorly soluble in water. The corresponding acetals of IPA and IPA derivatives may likewise be poorly soluble in water. In one or more embodiments of the invention, one or more solubility enhancing R groups may be included in an IPA acetal or IPA derivative acetal in order to increase the solubility in hydrophilic media, such as, for example, aqueous solutions. For instance, an acetal may be formed by reacting IPA with polyethylene glycol dialcohols to achieve acetals with improved water solubility. Due to the double functionality of both IPA and polyethylene glycol, simple mono-acetals, di-acetals, cyclic acetals, and even polymeric acetals may potentially be formed. In any event, the acetals may tend to have improved water solubility, due at least in part to the hydrophilic properties of the polyethylene glycol moiety. As one particular example, an IPA acetal solution may be prepared at a concentration that is greater than 1.0% (converted to IPA) in a 30% polyethylene glycol plus water solution, whereas the solubility of IPA in the same solution may be less than about 0.4%. In general, the approach is not limited to OPA or IPA, but may also optionally be applied to other acetals in order to increase their solubility.

These are just a few illustrative examples of the types of acetals that may be formed. The scope of the invention is not limited to just these types of acetals. In general, acetals may be formed from the numerous germicidal aromatic dialdehyde compounds disclosed above, as well as from other aromatic aldehydes having germicidal efficacy.

IV. Using Acetals to Increase Life of Germicidal Kits and/or Composition

Now, as previously described above in the background section, certain dialdehydes, such as, for example, OPA, may tend to oxidize over time to form carboxylic acids when exposed to air or oxygen and water. Over time, such as, for example, during prolonged periods of storage, such oxidation may consume the dialdehyde, which may tend to decrease the germicidal efficacy and/or lifetime of germicidal compositions.

Acetals tend to be less susceptible to oxidation reactions of the type mentioned in the background section than dialdehdyes. A germicidal kit or composition, according to one or more embodiments of the invention, may include an acetal that is capable of being converted to a germicidal aromatic dialdehyde compound. The acetal may be stored in the kit for a period of time, such as, for example, from several days, to a week, to a month, to several months, or more, without significant oxidative losses. The oxidative losses should at least be less than what would be expected for a dialdehyde stored over the same period of time. In this way, the acetal may help to increase the shelf life and/or use life of the kit and/or composition. The acetal may then be converted to the germicide, either gradually over time, or at an appropriate time, such as, for example, at or near an intended time of use of the kit and/or composition for sterilization and/or disinfection. In one aspect, the acetal or composition thereof may be added as a water-dry solid or water-dry liquid form, or other form that may help to postpone hydrolysis during storage, into an aqueous medium, such as, for example, an aqueous solution. The acetal may be hydrolyzed in the aqueous medium to form germicidal aromatic dialdehyde. pH adjustment may optionally be performed to lower the pH of the aqueous medium in order to catalyze or otherwise promote hydrolysis of the acetal.

V. Using Acetals to Add Germicidal to Deployed Germicidal Solutions

The inventors have also recognized that the concentration of germicide in a deployed germicidal solution may tend to change, often decrease, over time. In common practice, the germicidal solution may be used repeatedly for disinfection of endoscopes and other medical equipment over a prolonged period, such as, for example, ranging from several weeks to over a month. During this period of time, the concentration of the germicide may tend to decrease due to a variety of potential causes. Representative causes include, but are not limited to, oxidation and potentially other reactive conversions, sorption to endoscopes and other medical equipment and removal from the system. Additionally, endoscopes and other medical equipment treated with the composition may tend to carry water into the composition, which may tend to dilute or reduce the concentration of the germicide. In some cases, it may be advantageous to maintain a substantially constant concentration, or at least maintain the concentration at or above a minimum effective concentration.

According to one or more embodiments of the invention, acetal may be added to a deployed germicidal solution, either all at once, or periodically, and may be reactively converted to germicidal aromatic dialdehyde within the deployed germicidal solution. In one particular embodiment of the invention, acetal may be added to the germicidal solution and hydrolyzed gradually over a typical, expected, or recommended lifetime of the germicidal solution. For example, in one or more embodiments of the invention, the acetal may be hydrolyzed at a rate that is sufficient to substantially offset losses in germicidal efficacy and/or maintain the germicidal solution at a substantially constant germicidal efficacy. In one aspect, the rate may be set or controlled by setting or controlling a pH. The amount of acetal converted may optionally be based on historically experienced losses or otherwise estimated. Advantageously, the acetal may be used to replenish gradual losses of the germicidal aromatic dialdehyde and/or to stabilize or maintain a particular concentration of the germicidal aromatic dialdehyde in the solution.

VI. Germicidal Solutions and Compositions

The employed germicidal compositions disclosed herein may include the germicidal aromatic dialdehyde and/or one or more other germicides at a germicidally effective concentration that is suitable for the particular implementation. Often, the germicidally effective concentration may range from about 0.025% to a saturation concentration.

For example, phthalaldehyde may be used in the composition at an in-use concentration of from 0.025% to 2.0%, or 0.1 to 1% by weight. Higher concentrations, for example, up to 5%, or a saturation concentration, may be used if desired. Higher concentrations of phthalaldehyde may be used for shipping the composition to the point of use, and then composition may be diluted with water to the desired use concentration. The solubility of phthalaldehyde in water is about 5% by weight, which may be increased by including a water miscible, or at least more water-soluble, co-solvent. Suitable solvents include methanol, ethanol, isopropanol, n-butanol, t-butanol, glycols, tetrahydrofuran, dimethylsulfoxide and dioxane, among others.

To achieve good disinfection or sterilization, it may be appropriate to provide an in-use pH of from about 6 to 10, about 6 to 9, about 7 to 8, or in some cases from about 7.2 to 7.7. Even higher pH up to about 11 may be employed, although such high or alkaline pH may potentially damage certain materials, such as rubber, during disinfection or sterilization. In certain cases, depending upon the application, it may be appropriate to maintain an in-use pH that is less than 9, or more often less than 10, to provide greater compatibility with rubber and other materials.

Acids, bases, buffers or other pH adjusters may optionally be employed for any desired pH adjustment. The pH adjusters may be present in a sufficient amount, for example 0.05 wt % to 2.5 wt %, to give a desired pH. Examples of suitable pH adjusters or buffers that may be employed in the germicidal composition include, but are not limited to, sodium hydroxide (NaOH) plus hydrochloric acid, borax plus HCl, carbonate plus hydrogen carbonate, diethylbarbiturate (veronal) and HCl, $KH_2PO_4$ plus borax, N-2-hydoxythylpiperazine-N'-2-ethanesulfonic acid and NaOH, and phosphate. Still another exemplary pH adjuster is a phosphate buffer, such as the $KH_2PO_4$ and $Na_2HPO_4$ phosphate buffer, which is able to buffer a pH in a range from about 6 to 7.5. Another exemplary pH adjuster is EDTA (ethylenediaminetetraacetic acid) in a free acid, mono-, di-, tri-, or tetra-salt form, or a buffer including a combination of such forms, which allow buffering over a pH range from about 3 to 10. The EDTA may also serve as a chelating agent to help prevent precipitation. For example, other alkalinating or acidifying agents, such as organic carboxylate salts (e.g., sodium citrate, sodium acetate, potassium hydrogen phthalate, potassium citrate, potassium acetate), inorganic borate salts (e.g., potassium borate or sodium borate), and mixtures of such agents, may potentially be employed. It will be appreciated that such buffers may also optionally be employed in the other compositions disclosed herein. The pH adjusters may be present in a sufficient amount, for example 0.05 wt % to 2.5 wt %, to give a desired pH.

The compositions disclosed herein may optionally contain chelating agents, corrosion inhibitors, surfactants, dyes, fragrances, and other desired components. The components may be employed in amounts appropriate to achieve the desired chelating, corrosion inhibition, coloring, or other effect.

Examples of suitable chelating agents that may be employed in the germicidal composition include, but are not limited to, BDTA (N,N'-1,4-butanediylbis[N-(carboxymethyl)] glycine), EDTA, various ionized forms of EDTA, EGTA (N"-ursodeoxycholyl-diethylenetriamine-N,N,N'-triacetic acid), PDTA (N,N'-1,3-propanediylbis[N-(carboxymethyl)] glycine), TTHA (3,6,9,12-Tetraazatetradecanedioic acid, 3,6,9,12-tetrakis(carboxymethyl)), trisodium HEDTA (N-[2[bis(carboxymethyl)amino]ethyl]-N-(2-hydroxyethyl)-glycine, trisodium salt), sometimes known as Versenol 120. Numerous other chelating agents known in the arts may also optionally be employed.

Examples of suitable corrosion inhibitors that may be employed in the germicidal composition include, but are not limited to, ascorbic acid, benzoic acid, benzoimidazole, citric acid, 1H-benzotriazole, 1-hydroxy-1H-benzotriazole, phosphate, phosphonic acid, pyridine, and sodium benzoate. Numerous other corrosion inhibitors known in the arts may also optionally be employed.

Examples of suitable dyes that may be employed in the germicidal composition include, but are not limited to, Blue 1 (Brilliant Blue FCF) if a bluish color is desired, D&C Green No. 5, D&C Green No. 6, and D&C Green No. 8, if a greenish color is desired, Yellow No. 5 if a yellowish color is desired, etc. Numerous other dyes known in the arts may also optionally be employed.

VII. Germicidal Kits

The inventors have developed germicidal containers and kits that may be used to contain, store, and distribute ingredients for preparing germicidal solutions. The kits may include multiple compartments, either in the same container or in different containers. The containers may include cans, tanks, bottles, boxes, bags, canisters, pouches, or other rigid or flexible containers known in the arts.

Figure 1:
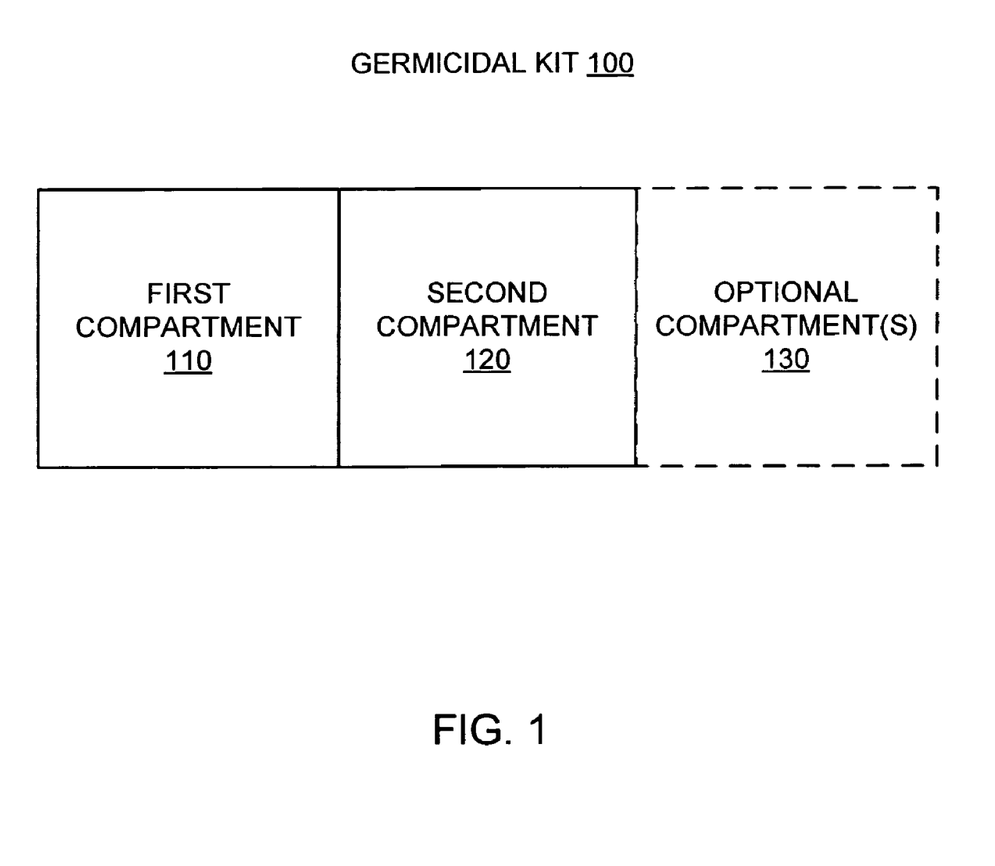
FIG. 1 shows an exemplary germicidal kit, according to one or more embodiments of the invention.

FIG. 1 shows an exemplary germicidal kit 100, according to one or more embodiments of the invention. The illustrated kit includes a first compartment 110, a second compartment 120, and optionally one or more other compartments 130. As previously discussed, compartments may either be in the same container or in different containers, or some may be in the same container and others may be in different containers. The first and second compartments may be physically separated and distinct to completely separate their contents.

In one or more embodiments of the invention, the compartments may contain a germicidal aromatic dialdehyde, and an acetal that is capable of hydrolyzing to form a germicidal compound, such as, for example, either the same or a different type of germicidal aromatic dialdehyde. By way of example, the germicidal aromatic dialdehyde may be included in one of the compartments and the acetal may be included in another different compartment.

The germicidal aromatic dialdehyde may often be included as either a solution or as a dry solid. If the germicidal aromatic dialdehyde is included as a dry solid, then another compartment may optionally include a solvent, such as, for example, an aqueous solution with one or more other ingredients, such as, for example, pH adjusters, which may be used to prepare a germicidal solution from the dry solid.

In one or more embodiments of the invention, the acetal may be provided in a form that is resistant to hydrolysis, such as, for example, as a dry solid, or as a liquid that lacks water. The dry solid may include a powder, flakes, or a shaped solid, for example. By way of example, the acetal may be included and sealed in a water impermeable or otherwise water resistant compartment, such as, for example, a metal (for example aluminum), plastic laminated metal, or plastic pouch or bag. The water resistant container may help to avoid entrance of water, or moisture, which may potentially prematurely promote conversion to aldehyde.

The compartment including the germicidal aromatic dialdehyde and the compartment including the acetal may each optionally include one or more other components. Suitable components possibly include, but are not limited to, water, solvents, pH adjusters, chelating agents (for example EDTA), corrosion inhibitors (for example benzotriazole), surfactants, germicidal efficacy enhancers, binder materials, dissolution enhancers, dyes, fragrances, and/or other components conventionally included in germicidal solutions. Water or other solvent may optionally be provided from another source, such as, for example, water may be provided from a tap at a point of use. However, these components may also or alternatively optionally be provide in one or more of the aforementioned optional additional compartments. In one aspect, ingredients that may potentially interact negatively with one another to optionally be provided in separate compartments. Still further, these additional components are all optional. Kits including only the germicidal aromatic dialdehyde compound and the acetal are contemplated.

When needed, a user or practitioner may obtain the container, such as, for example, from storage. In one aspect, the kit may allow the acetal to be stored for prolonged periods of time, such as, for example, for at least a month, for at least several months, for at least a yerar, without undergoing oxidation that may be experienced by an aldehyde. Commercially available OPA solutions available from the assignee of the present application generally have a shelf life of at least about two years. Generally, the concentration of the OPA decreases by no more than about 0.05% during a storage period of two years. So the kits may be stored for prolonged periods ranging from months to years.

A method, according to one or more embodiments of the invention, may include using a germicidal kit such as those described above to prepare a germicidal solution. As one example, each of the compartments may be opened, and then the contents or compositions of each of the compartments may be combined. Such a method may be performed by a user or practitioner, by an automated machine, such as, for example, an Automated Endoscope Reprocessor (AER), or portions of the method may be performed by the user and portions by the machine. A few illustrative possibilities will be described below, although the scope of the invention is not limited to just these possibilities.

In certain cases, the compartments may be capable of being opened separately. For example, one or more compartments may include a lid or other opening. As another example, one or more compartments may be cut open, torn open, or punctured, like a pouch or packet may be opened. In such cases, the contents of the compartments may optionally be removed or poured serially into a bucket, reservoir, processing basin, other portion of an AER, or other container, by the user or automated machine.

In some cases, the contents may be combined in a predetermined order. For example, the automated machine may first autonomously combine solvent of one compartment with germicide of another compartment. In the case of a multiple compartment container this may potentially include forming an opening in a wall between the compartments. Then, the machine may combine the resulting germicidal solution with acetal of another compartment. Then, the machine may introduce the resulting solution into a processing basin or other container.

As another option, the user or automated machine may flow water or other solvent serially through the compartments in a predetermined order and then remove the resulting solution to the processing basin or other container. Alternatively, the water or other solvent may be flowed through the compartments in parallel, either by the user or the automated machine.

In some cases, the contents of the compartments may be combined within the container. The kit may optionally include compartments that are coupled together by a mechanism to automatically mix the contents of the compartments, such as, for example, upon opening of the container. Such containers are known in the arts. An exemplary container that is suitable is disclosed in U.S. Pat. No. 5,540,326. This may also be achieved by forming an opening in the housing between the compartments, by rupture, tearing, opening a lid, etc. to combine the contents.

VIII. Methods of Using the Germicides and Germicidal Solutions

The germicides and germicidal compositions disclosed herein may be used as sterilants and/or disinfectants. A disinfectant generally refers to a material capable of killing all non-spore microbes but not spores. High-level disinfectant generally refers to a material capable of killing some spores, such as *Bacillus subtilis* and *Clostridium sporogenes*, in addition to killing non-spore microbes. A sterilant generally refers to a material capable of killing all spores and non-spores. Some of the compositions disclosed herein, such as, for example, certain compositions including OPA, may be able to kill highly resistant spores, such as, for example, *Bacillus subtilis* spores, as well as less resistant microbes, such as mycobacteria, nonlipid or small viruses, or fungi, in shorter times or with lower concentrations or temperatures.

A method of using the composition for disinfection or sterilization may include killing germs or other microorganisms by contacting the microorganisms, such as, for example, germs or spores, with the composition, or otherwise applying the composition to the microorganisms, either in the air, on surfaces, or in other fluids, in order to kill the microorganisms. The composition may be applied to the air by spraying, applied to a surface by immersion, spraying, coating, flowing, or the like, or applied to a fluid by combining the composition with the fluid, for example. Often, the composition may be employed to disinfect or sterilize a surface by contacting the surface with the composition, such as by immersion, spraying, coating, or flowing the composition over the surface for a period of time and at a temperature effective to achieve disinfection or sterilization of the surface. The composition may be employed manually, for example in a processing basin, or by an automated system, such as an automated endoscope reprocessor (AER). Generally, the solutions have the advantages of allowing disinfection or sterilization without expensive capital sterilization equipment, are easy for health personnel to use, and are effective and reliable.

As discussed above, loss of germicide in a deployed germicidal solution may potentially occur and/or dilution of the germicide may potentially occur. In one or more embodiments of the invention, the acetal as described above may be included in a deployed germicidal solution that may be employed in the basin of the AER or otherwise deployed. The acetal may gradually be converted to germicide, such as, for example, over the life of the solution. Advantageously, this may help to replenish loss of germicide and/or may help to stabilize or maintain an effective germicidal concentration. In one particular embodiment of the invention, the acetal may be used to maintain a minimum effective concentration of OPA in the germicidal solution that may be at least 0.3%, although the scope of the invention is not limited in this respect.

IX. EXAMPLES

Having been generally described, the following examples are given as particular embodiments of the invention, to illustrate some of the properties and demonstrate the practical advantages thereof, and to allow one skilled in the art to utilize the invention. It is understood that these examples are to be construed as merely illustrative, and not limiting.

Example 1

This example demonstrates how to prepare a 0.3% (w/v) phthalaldehyde germicidal solution. The solution was prepared by dissolving 0.3 g phthalaldehyde in de-ionized water, and then adding additional water make 100 milliliters (mL) solution. The phthalaldehyde was obtained from DSM Chemie Linz, located at St. Peter Strasse 25, P.O. Box 296, A-4021 Linz/Austria. When appropriate, the ingredients listed in the tables below were further included in phthalaldehyde solution in amounts appropriate to achieve solutions with the concentrations specified in the tables.

Example 2

This example demonstrates how to prepare an acetal, in particular OPA acetal, from a germicidal aromatic dialdehyde, in particular OPA, by using acidic catalysis. For example, OPA may be dissolved in a dry alcohol, such as, for example, methanol, ethanol, propanol, butanol, another short chain alkanol, glycol, or polyethylene glycol dialcohol. Next, an acid, such as, for example, sulfuric acid or trifluoroacetic acid, may be added to the mixture dropwise in order to achieve an acidic pH of about 2 to 3, for example. The acid may serve as a catalyst for the reaction in which the OPA reacts with the alcohol to form OPA acetal. The resulting mixture may then be stirred at about room temperature for a period of about four hours in order to allow the reaction to proceed. Longer times may be appropriate if the pH is greater than 3, such as from 3 to 5. Then, a base, such as, for example, a dilute aqueous sodium carbonate ($Na_2CO_3$) solution, may be added to the mixture, in order to quench or slow the reaction. Next, the mixture may be extracted with ethyl acetate or an ether, such as, for example, diethyl ether. During the extraction, the OPA acetal may be extracted from the alcohol solution into the ether solution. The resulting ether solution, which may include the OPA acetal, may be dried, such as, for example, with sodium sulfate. Then, the ether may be removed by evaporation at room temperature with a vacuum in order to yield OPA acetal. Many other germicidal aromatic dialdehydes may be converted into their corresponding acetals by reaction with anhydrous alcohols at room temperature under acidic conditions using analgous adapted procedures.

Example 3

This example demonstrates that various acetals may be converted to the germicidal aromatic dialdehyde OPA. The reactions of 1,3-dimethoxyphthalan, 1,3-diethoxyphthalan, a PEG 200 pegylated OPA acetal at various pH in distilled water were evaluated at room temperature. The acetals were suspended in distilled water, followed by pH measurement, and pH adjustment with either hydrogen chloride (HCl), phthalic acid, or sodium hydroxide (NaOH), depending on the particular pH. The mixture was stirred at room temperature and monitored by gas chromatograph/mass spectroscopy (GC/MS) at various time intervals. The results are shown in Tables 1 through 5.

TABLE 1

Hydrolysis of 1,3-dimethoxyphthalan (33.9 mg, 0.001 mole equivalents of phthalic acid, water 5.8 mL, pH = 5.0)

| | Time (h) | | | | | | |
|---|---|---|---|---|---|---|---|
| | 0 | 24 | 120 | 240 | 360 | 480 | 576 |
| OPA recovery (%)[1] | 0 | 6.4 | 38.6 | 70.1 | 85.3 | 94.2 | 97.1 |
| OPA (w/w %)[2] | 0.000 | 0.028 | 0.166 | 0.301 | 0.367 | 0.405 | 0.417 |

[1]OPA recovery (%) is the GC area percentage of OPA converted from the acetal relative to total GC area of OPA and acetal. OPA recovery (%) = 100 * (OPA area)/(OPA area + Acetal area)
[2]OPA w % is the percentage of OPA in the solution. It is calculated as: OPA w % = (OPA GC area %) * (acetal wt) * 134/(Acetal MW)/[(water wt) + (acetal wt)], where 134 is the molecular weight of OPA, and Acetal MW is the molecular weight of acetal, which is 180.

TABLE 2

Hydrolysis of 1,3-diethoxyphthalan (33 mg, pH = 5.4, HCl adjusted, water 3.5 mL)

| | Time (h) | | | | | | |
|---|---|---|---|---|---|---|---|
| | 0 | 2 | 48 | 120 | 240 | 360 | 480 |
| OPA recovery (%)[1] | 0 | 4.0 | 9.3 | 26.2 | 49.2 | 87.3 | 99.0 |
| OPA (w/w %)[2] | 0.000 | 0.024 | 0.056 | 0.158 | 0.296 | 0.525 | 0.596 |

[1]OPA recovery (%) is the GC area percentage of OPA converted from the acetal relative to total GC area of OPA and acetal. OPA recovery (%) = 100 * (OPA area)/(OPA area + Acetal area)
[2]OPA w % is the percentage of OPA in the solution. It is calculated as: OPA w % = (OPA GC area %) * (acetal wt) * 134/(Acetal MW)/[(water wt) + (acetal wt)], where 134 is the molecular weight of OPA, and Acetal MW is the molecular weight of acetal, which is 208.

TABLE 3

Hydrolysis of 1,3-diethoxyphthalan 31 mg, pH = 6.9, water 4 mL)

| | Time (h) | | | | | | |
|---|---|---|---|---|---|---|---|
| | 0 | 1 | 20 | 144 | 240 | 359 | 480 |
| OPA recovery (%)[1] | 0 | 0.0 | 2.0 | 19.6 | 41.1 | 84.5 | 96.0 |
| OPA (w/w %)[2] | 0.000 | 0.000 | 0.010 | 0.097 | 0.204 | 0.419 | 0.476 |

[1]OPA recovery (%) is the GC area percentage of OPA converted from the acetal relative to total GC area of OPA and acetal. OPA recovery (%) = 100 * (OPA area)/(OPA area + Acetal area)
[2]OPA w % is the percentage of OPA in the solution. It is calculated as: OPA w % = (OPA GC area %) * (acetal wt) * 134/(Acetal MW)/[(water wt) + (acetal wt)], where 134 is the molecular weight of OPA, and Acetal MW is the molecular weight of acetal, which is 208.

TABLE 4

Hydrolysis of 1,3-diethoxyphthalan (22.4 mg,
pH = 10.8, NaOH adjusted, water 3 mL)

| | Time (h) | | | | |
|---|---|---|---|---|---|
| | 48 | 120 | 480 | 720 | 960 |
| OPA recovery (%)[1] | 1.0 | 1.3 | 9.9 | 23.4 | 47.9 |
| OPA (w/w %)[2] | 0.0048 | 0.0062 | 0.0473 | 0.112 | 0.229 |

[1]OPA recovery (%) is the GC area percentage of OPA converted from the acetal relative to total GC area of OPA and acetal. OPA recovery (%) = 100 * (OPA area)/(OPA area + Acetal area)

[2]OPA w % is the percentage of OPA in the solution. It is calculated as: OPA w % = (OPA GC area %) * (acetal wt) * 134/(Acetal MW)/[(water wt) + (acetal wt)], where 134 is the molecular weight of OPA, and Acetal MW is the molecular weight of acetal, which is 208.

TABLE 5

Hydrolysis of a PEG 200 pegylated OPA acetal (0.50 g of mixture including
PEG 200 pegylated OPA acetal from 0.08759 g of OPA, pH = 6.3, water 20 mL)

| | Time (h) | | | | | | | |
|---|---|---|---|---|---|---|---|---|
| | 0 | 120 | 240 | 360 | 480 | 600 | 840 | 1032 |
| OPA recovery (%)[3] | 0 | 4.2 | 18.0 | 37.0 | 49.0 | 61.2 | 82.8 | 96.7 |
| OPA (w/w %) | 0 | 0.018 | 0.079 | 0.162 | 0.215 | 0.268 | 0.363 | 0.424 |

[3]OPA recovery (%) was obtained based on internal standard (naphthalene)

This example demonstrates that various acetals may be converted to the germicidal aromatic dialdehyde OPA. The hydrolysis rate depends upon pH. Over the range of pH investigated, the lower the pH, the faster the hydrolysis rate.

Example 4

This example demonstrates that 1,3-diethoxyphthalan may be converted to the germicidal aromatic dialdehyde OPA in the presence of OPA. The hydrolysis of 1,3-diethoxyphthalan in the presence of OPA in distilled water at various pH was evaluated at room temperature. 1,3-Diethoxyphthalan was added to the OPA solution in distilled water, followed by pH measurement and adjustment with either HCl or NaOH, depending on the pH. The mixtures were stirred at room temperature and monitored by GC/MS at various time intervals. The results are shown in Tables 6 through 8.

TABLE 6

Hydrolysis of 1,3-diethoxyphthalan (22.2 mg) in the presence of OPA (111 mg,
pH = 8.9, NaOH adjusted, water 22.2 mL)

| | Time (h) | | | | | | | | | |
|---|---|---|---|---|---|---|---|---|---|---|
| | 0 | 96 | 240 | 336 | 480 | 600 | 720 | 840 | 960 | 1200 |
| OPA %[4] | 78.2 | 78.6 | 81.2 | 82.8 | 86.2 | 89.0 | 93.3 | 95.4 | 97.0 | 98.8 |
| Acetal %[4] | 21.8 | 21.4 | 18.8 | 17.2 | 13.8 | 11.0 | 6.7 | 4.6 | 3.0 | 1.2 |
| OPA (w %)[5] | 0.498 | 0.498 | 0.507 | 0.511 | 0.521 | 0.530 | 0.542 | 0.548 | 0.553 | 0.558 |

[4]The OPA and acetal percentages are calculated from GC areas. OPA % = 100 * (OPA area)/[(OPA area) + (acetal area)] Acetal % = 100 * (acetal area)/[(OPA area) + (acetal area)]

[5]OPA w % is calculated from the initial OPA quantity and acetal conversion estimated from its GC area percentage change at the time. OPA w % = 100 * [(initial OPA wt) + (initial acetal % − acetal %) * (initial acetal wt) * 134/208/(initial acetal %)]/[(water wt) + (OPA wt) + (acetal wt)]
Sample calculation for Table 6 at 10 days: OPA w % = 100 * [(0.111) + (21.8 − 18.8) * (0.0222) * 134/208/(21.8)]/(22.2 + 0.111 + 0.0222) = 0.507

TABLE 7

Hydrolysis of 1,3-diethoxyphthalan (21.9 mg) in the presence of OPA (110 mg, pH = 8.0, NaOH adjusted, water 22 mL)

| | Time (h) | | | | | | | | |
|---|---|---|---|---|---|---|---|---|---|
| | 0 | 48 | 144 | 240 | 312 | 480 | 576 | 720 | 840 | 960 |
| OPA %[4] | 79.1 | 78.4 | 81.4 | 83.0 | 84.8 | 89.6 | 91.9 | 96.6 | 98.0 | 99.0 |
| Acetal %[4] | 20.9 | 21.6 | 18.6 | 17 | 15.2 | 10.4 | 8.1 | 3.4 | 2 | 1 |
| OPA (w %)[5] | 0.498 | 0.496 | 0.505 | 0.510 | 0.515 | 0.530 | 0.537 | 0.551 | 0.555 | 0.558 |

[4]The OPA and acetal percentages are calculated from GC areas. OPA % = 100 * (OPA area)/[(OPA area) + (acetal area)] Acetal % 100 * (acetal area)/[(OPA area) + (acetal area)]
[5]OPA w % is calculated from the initial OPA quantity and acetal conversion estimated from its GC area percentage change at the time. OPA w % = 100 * [(initial OPA wt) + (initial acetal % − acetal %) * (initial acetal wt) * 134/208/(initial acetal %)]/[(water wt) + (OPA wt) + (acetal wt)]
Sample calculation for Table 6 at 10 days: OPA w % = 100 * [(0.111) + (21.8 − 18.8) * (0.0222) * 134/208/(21.8)]/(22.2 + 0.111 + 0.0222) = 0.507

TABLE 8

Hydrolysis of 1,3-diethoxyphthalan (22.3 mg) in the presence of OPA (111 mg, pH = 6.95, NaOH adjusted, water 22.2 mL)

| | Time (h) | | | | | | | |
|---|---|---|---|---|---|---|---|---|
| | 0 | 48 | 120 | 168 | 240 | 312 | 480 | 552 |
| OPA %[4] | 78.2 | 81.9 | 87.9 | 90.6 | 93.6 | 95.8 | 98.8 | 99.3 |
| Acetal %[4] | 21.8 | 18.1 | 12.1 | 9.4 | 6.4 | 4.2 | 1.2 | 0.7 |
| OPA (w %)[5] | 0.498 | 0.509 | 0.527 | 0.535 | 0.543 | 0.550 | 0.559 | 0.560 |

[4]The OPA and acetal percentages are calculated from GC areas. OPA % = 100 * (OPA area)/[(OPA area) + (acetal area)] Acetal % = 100 * (acetal area)/[(OPA area) + (acetal area)]
[5]OPA w % is calculated from the initial OPA quantity and acetal conversion estimated from its GC area percentage change at the time. OPA w % = 100 * [(initial OPA wt) + (initial acetal % − acetal %) * (initial acetal wt) * 134/208/(initial acetal %)]/[(water wt) + (OPA wt) + (acetal wt)]
Sample calculation for Table 6 at 10 days: OPA w % = 100 * [(0.111) + (21.8 − 18.8) * (0.0222) * 134/208/(21.8)]/(22.2 + 0.111 + 0.0222) = 0.507

This example demonstrates that 1,3-diethoxyphthalan may be converted to the germicidal aromatic dialdehyde OPA in the presence of OPA. Over the range of pH investigated, the hydrolysis rate increases with decreasing pH.

Example 5

This example demonstrates that the tetramethyl acetal of IPA may be converted to IPA. The process takes place in two staged reactions. In one experiment, the tetramethyl acetal of IPA (0.114 g, 0.504 mmol) was suspended in 100 mL of water including 67 mg of OPA as the internal standard. A relatively large volume of water was used due to the low solubility of IPA. The pH of the water was adjusted to 4.34 with 1% HCl. At various time intervals 0.5 mL of the reaction mixture was sampled and extracted with 1 mL of ethyl acetate (EtOAc). The samples were analyzed with gas chromatography. Thin liquid chromatography and gas chromatography were used to show that finally all of the acetal was converted to IPA. The results are shown in Table 9.

TABLE 9

IPA and acetal compositions during hydrolysis

| | | Time (h) | 8 | 32 | 54 |
|---|---|---|---|---|---|
| Mole %[6] | IPA | | 20.3 | 66.1 | 100 |
| | Monoacetal | | 79.7 | 33.9 | 0 |
| | Acetal | | 0 | 0 | 0 |

TABLE 9-continued

IPA and acetal compositions during hydrolysis

| | | Time (h) | 8 | 32 | 54 |
|---|---|---|---|---|---|
| wt % | IPA | | 0.014 | 0.045 | 0.068 |
| | Monoacetal | | 0.091 | 0.039 | 0 |

[6]Mole % was calculated based on the initial amount of acetal (114 mg, 0.504 mmol) and OPA (67 mg) as internal standard.

This example demonstrates that the tetramethyl acetal of IPA may be converted to IPA. The diacetal starting material disappeared within 8 h, but hydrolysis of the second acetal group of the monoacetal took longer period of time. This indicating that the first acetal functionality was converted to aldehyde much faster than second acetal functionality. Full conversion to IPA was achieved in about 54 hours.

Example 6

This example demonstrates that a pegylated acetal of IPA may be converted to IPA in aqueous solution. 2.18 g of a PEG 200 pegylated acetal solution in PEG, including the acetal from 72.2 mg of IPA, was dissolved in 10 mL of diluted sodium carbonate ($Na_2CO_3$) (1 mL saturated $Na_2CO_3$ and 9 mL water) and a clear colorless solution was obtained. The pH of this solution was adjusted to 1.41 with HCl and the hydrolysis was performed with stirring at room temperature. White crystal appeared in about 5 minutes. The reaction was stirred overnight and thin liquid chromatography confirmed that all the pegylated acetal of IPA was hydrolyzed to IPA. The IPA was extracted with ethyl acetate (3×7 mL). The IPA solution-in ethyl acetate was dried with magnesium sulfate. The crude material was purified with a silica column (1.4×8 cm, solvent 1/1 hexane-EtOAc). Clean IPA product was obtained (68 mg) in a 94% recovery.

X. Other Matters

In the description above, for the purposes of explanation, numerous specific details are set forth in order to provide a thorough understanding of the embodiments of the invention. It will be apparent, however, to one skilled in the art that another embodiment may be practiced without some of these specific details. In other instances, well-known structures, devices, and techniques have been shown in block diagram form or without detail in order not to obscure the understanding of this description.

Many of the methods are described in their most basic form, but operations may be added to or deleted from any of the methods without departing from the basic scope of the invention. It will be apparent to those skilled in the art that many further modifications and adaptations may be made. The particular embodiments are not provided to limit the invention but to illustrate it. The scope of the invention is not to be determined by the specific examples provided above but only by the claims below.

It should also be appreciated that reference throughout this specification to "one embodiment" or "an embodiment" means that a particular feature may be included in the practice of the invention. Similarly, it should be appreciated that in the foregoing description of exemplary embodiments of the invention, various features are sometimes grouped together in a single embodiment, Figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

In the claims, any element that does not explicitly state "means for" performing a specified function, or "step for" performing a specified function, is not to be interpreted as a "means" or "step" clause as specified in 35 U.S.C. Section 112, Paragraph 6. In particular, the use of "step of" in the claims herein is not intended to invoke the provisions of 35 U.S.C. Section 112, Paragraph 6.

While the invention has been described in terms of several embodiments, those skilled in the art will recognize that the invention is not limited to the embodiments described, but may be practiced with modification and alteration within the spirit and scope of the appended claims. The description is thus to be regarded as illustrative instead of limiting.

What is claimed is:

1. A method comprising:
   adding an acetal to a germicidal solution;
   forming a dialdehyde by gradually hydrolyzing the acetal within the germicidal solution over at least 48 hours after the germicidal solution has been deployed; and
   contacting medical equipment with the germicidal solution including the acetal.

2. The method of claim 1, further comprising hydrolyzing the acetal gradually over a lifetime of the germicidal solution.

3. The method of claim 1, further comprising hydrolyzing the acetal at a rate that is sufficient to substantially offset losses in germicidal efficacy and maintain the germicidal solution at a substantially constant germicidal efficacy.

4. The method of claim 1, further comprising, prior to said forming the dialdehyde, storing the acetal for at least a week, and wherein said hydrolyzing the acetal is initially performed at an intended time of use of the germicidal solution to kill the germs.

5. The method of claim 1, wherein said adding the acetal comprises adding a powder or liquid of the acetal, and wherein the germicidal solution includes water and a germicidal aromatic dialdehyde.

6. The method of claim 1, wherein said forming the dialdehyde comprises forming a germicidal aromatic dialdehyde that is selected from the group consisting of orthophthalaldehyde (OPA), isophthalaldehyde (IPA), terephthalaldehyde (TPA), 4-halo-phthalaldehydes, phenylpropanedial, 3-(1-formyl-2-oxoethyl)-2-nitro-benzoic acid, 4-pyrimidinyl-propanedial, 2-benzoxazolyl-propanedial, (4-methoxyphenyl)-propanedial, and 2-pyridinyl-propanedial.

7. The method of claim 6, wherein said forming the germicidal aromatic dialdehyde comprises forming one or more of OPA and IPA.

8. The method of claim 6, wherein the solution initially includes a germicide before said hydrolysis.

9. A composition comprising:
   a germicidal aromatic dialdehyde;
   an acetal that is capable of hydrolyzing to form a germicidal compound; and
   a corrosion inhibitor, wherein the composition has a pH of at least 7.2.

10. The composition of claim 9, wherein the germicidal aromatic dialdehyde is selected from the group consisting of orthophthalaldehyde (OPA), isophthalaldehyde (IPA), terephthalaldehyde (TPA), 4-halo-phthalaldehydes, phenylpropanedial, 3-(1-formyl-2-oxoethyl)-2-nitro-benzoic acid, 4-pyrimidinyl-propanedial, 2-benzoxazolyl-propanedial, (4-methoxyphenyl)-propanedial, and 2-pyridinyl-propanedial.

11. The composition of claim 10, wherein the germicidal aromatic dialdehyde comprises one or more of OPA and IPA.

12. The composition of claim 9, wherein the acetal comprises an aromatic acetal that is capable of hydrolyzing to form a germicidal aromatic dialdehyde.

13. The composition of claim 12, wherein the acetal comprises a 1,3-dialkoxyphthalalan.

14. The composition of claim 9, wherein the acetal comprises a solubility enhancing polymeric moiety.

15. The composition of claim 9, wherein the acetal is pegylated.

16. The composition of claim 9, further comprising:
   a pH adjuster;
   a chelating agent; and
   a surfactant.

17. The composition of claim 16, further comprising:
   a buffer;
   a corrosion inhibitor;
   a fragrance; and
   a coloring agent.

18. A method comprising killing microorganisms by applying the composition of claim 9 to the microorganisms.

19. A kit comprising:
   a germicidal aromatic dialdehyde;
   an acetal that is capable of hydrolyzing to form a germicidal compound;

at least two compartments to contain the germicidal aromatic dialdehyde and the acetal.

20. The kit of claim 19, wherein the germicidal aromatic dialdehyde is included in a first compartment with water, and wherein the acetal is included substantially dry in a second compartment.

21. The kit of claim 19, further comprising a mechanism to mix the contents of the at least two compartments.

22. The kit of claim 19:
wherein the germicidal aromatic dialdehyde is selected from the group consisting of orthophthalaldehyde (OPA), isophthalaldehyde (IPA), terephthalaldehyde (TPA), 4-halo-phthalaldehydes, phenyl-propanedial, 3-(1-formyl-2-oxoethyl)-2-nitro-benzoic acid, 4-pyrimidinyl-propanedial, 2-benzoxazolyl-propanedial, (4-methoxyphenyl)-propanedial, and 2-pyridinyl-propanedial; and
wherein the acetal comprises an aromatic acetal that is capable of hydrolyzing to form a germicidal aromatic dialdehyde.

23. The kit of claim 19, further comprising at least six components selected from the group consisting of a pH adjuster, a chelating agent, a surfactant, a buffer, a corrosion inhibitor, a fragrance, a coloring agent, which are included in the at least two compartments.

24. The method of claim 1, further comprising, after said contacting the medical equipment with the germicidal solution:
adding additional acetal to the solution that was used to contact the medical equipment; and forming additional germicidal aromatic dialdehyde by hydrolyzing the additional acetal.

25. The method of claim 1, wherein said forming the dialdehyde comprises forming an aromatic dialdehyde.

26. The method of claim 1, wherein said forming the dialdehyde comprises forming a germicidal dialdehyde.

27. The method of claim 1, further comprising hydrolyzing the acetal within the deployed germicidal solution gradually over at least 120 hours.

28. The method of claim 1, wherein forming the dialdehyde comprises forming the dialdehyde in a solution having a pH of from 7.2 to 7.7.

29. The method of claim 1, wherein the acetal comprises a solubility enhancing polymeric moiety.

30. The method of claim 1, wherein the acetal is pegylated.

31. The composition of claim 9, wherein the composition has a pH of from 7.2 to 7.7.

32. The kit of claim 19, wherein the germicidal aromatic dialdehyde is selected from OPA and IPA, and wherein the acetal is capable of hydrolyzing to form one of OPA and IPA.

33. The kit of claim 19, wherein the acetal comprises a solubility enhancing polymeric moiety.

34. The kit of claim 19, wherein the acetal is pegylated.

35. The method of claim 1, wherein adding the acetal comprises adding the acetal to a deployed germicidal solution.

36. The method of claim 1, wherein adding the acetal to the germicidal solution comprises adding the acetal to a germicidal solution in a basin of an automated endoscope reprocessor.

37. The composition of claim 9, wherein the pH is sufficient to allow gradual hydrolysis of the acetal over at least 48 hours.

38. The composition of claim 37, wherein the pH is sufficient to allow gradual hydrolysis of the acetal over at least 120 hours.

* * * * *